(12) United States Patent
Miller et al.

(10) Patent No.: US 6,737,029 B2
(45) Date of Patent: May 18, 2004

(54) METHOD AND APPARATUS FOR STERILIZING MAIL

(76) Inventors: Jimmie D. Miller, 1304 N. 8th St., Arkansas City, KS (US) 67005-2038; Blair Sutton, P.O. Box 418, Lawrence, KS (US) 66067

( * ) Notice: Subject to any disclaimer, the term of this patent is extended or adjusted under 35 U.S.C. 154(b) by 0 days.

(21) Appl. No.: 10/223,919

(22) Filed: Aug. 20, 2002

(65) Prior Publication Data

US 2003/0129111 A1 Jul. 10, 2003

Related U.S. Application Data

(60) Provisional application No. 60/337,648, filed on Dec. 7, 2001.

(51) Int. Cl.$^7$ ................ A61L 2/14; A61L 2/00
(52) U.S. Cl. ............ 422/300; 422/292; 422/305; 422/186.07; 232/30
(58) Field of Search ............... 422/1, 22, 23, 422/29, 28, 186.07, 186.08, 24, 292, 300, 305, 306; 232/31, 30; 382/101; 73/863.22; 209/509, 900

(56) References Cited

U.S. PATENT DOCUMENTS

| | | | |
|---|---|---|---|
| 3,718,082 A | 2/1973 | Lipoma | |
| 4,485,308 A | * 11/1984 | Rabatin | 250/461.1 |
| 4,877,964 A | 10/1989 | Tanaka et al. | |
| 4,923,681 A | 5/1990 | Cox et al. | |
| 5,374,814 A | 12/1994 | Kako et al. | |
| 5,879,732 A | * 3/1999 | Caracciolo et al. | 426/231 |
| 5,917,925 A | * 6/1999 | Moore | 382/101 |
| 5,958,336 A | 9/1999 | Duarte | |
| 6,048,493 A | 4/2000 | Melgarrd et al. | |
| 6,090,346 A | 7/2000 | Rose et al. | |
| 6,152,001 A | * 11/2000 | Faustmann | 83/30 |
| 6,228,330 B1 | 5/2001 | Herrmann et al. | |
| 6,284,193 B1 | * 9/2001 | Carman et al. | 422/33 |
| 2002/0124664 A1 | * 9/2002 | Call et al. | 73/863.22 |
| 2002/0150500 A1 | * 10/2002 | Carman et al. | 422/28 |
| 2003/0086818 A1 | * 5/2003 | Holley et al. | 422/24 |
| 2003/0086821 A1 | * 5/2003 | Matthews | 422/29 |
| 2003/0103866 A1 | * 6/2003 | Wang et al. | 422/24 |
| 2003/0127506 A1 | * 7/2003 | Braun, Jr. | 232/31 |
| 2003/0138345 A1 | * 7/2003 | Schwabe | 422/22 |
| 2003/0145664 A1 | * 8/2003 | Schwarz et al. | 73/863.22 |

\* cited by examiner

*Primary Examiner*—Robert J. Warden, Sr.
*Assistant Examiner*—Sean E. Conley
(74) *Attorney, Agent, or Firm*—Dale J. Ream

(57) ABSTRACT

An apparatus for sterilizing an article of mail includes a chamber defining an airtight space and having an entrance for receiving the article of mail. A vacuum pump is coupled to the chamber for withdrawing air therefrom and, specifically, from the article of mail, this air withdrawal reducing the chamber air pressure. An ozone generator is coupled to the chamber for introducing ozone at atmospheric pressure therein following air withdrawal. This causes efficient diffusing of the ozone into the article of mail for sterilizing it against anthrax. The ozone is then withdrawn into an ozone filter that includes a non-consumable manganese dioxide catalyst for converting the ozone back into oxygen. The article of mail may be initially perforated to enhance air withdrawal and ozone diffusion. The article of mail may be embossed following ozone withdrawal to indicate completion of sterilization. The apparatus may be implemented using multiple chambers.

10 Claims, 4 Drawing Sheets

METHOD AND APPARATUS FOR STERILIZING MAIL

CROSS REFERENCE TO RELATED APPLICATIONS

This application claims the benefit of U.S. Provisional Application No. 60/337,648, filed Dec. 7, 2001, entitled Device To Sterilize Anthrax Spores Being Sent Thru The Mail.

BACKGROUND OF THE INVENTION

This invention relates to decontamination and sterilization devices and, more particularly, to a method and apparatus for sterilizing articles of mail that may be tainted with anthrax or other pathogens.

A single letter contaminated with anthrax or similar pathogens can cause serious health issues or even death to humans. In fact, a single letter may include thousands of times more than the lethal dose of anthrax. The threat of safety relative to the delivery of mail was accented by the anthrax infections following the historic terrorist attacks against the United States on Sep. 11, 2001. Several people were infected with anthrax as a result of letters containing the deadly pathogens. Postal offices and other businesses had to be shut down and fully sterilized. Anthrax in a single letter can cross-contaminate other articles of mail, postal sorting equipment, and the like. This is a significant problem in view of the 680 million pieces of mail handled by the U.S. Postal Service every day.

Various devices have been proposed for sterilizing medical equipment and other articles. Although assumably effective for their intended purposes, the existing devices are not suitable for sterilizing mail at the initial point of mail deposit or without damaging the mail. More particularly, the use of steam heat or intense dry heat would irreversibly damage mail. Further, chemical sterilization with ethylene oxide gas avoids the damages associated with heat sterilization but requires long cycle times and the handling of harsh chemicals. These disadvantages would be unacceptable for use in mass mail processing. Sterilization with gamma radiation, while effective, would be prohibitively expensive for use in the decentralized mail processing and delivery industry.

Therefore, it is desirable to have a method and apparatus for sterilizing mail quickly and without damaging the mail. Further, it is desirable to have a method and apparatus for sterilizing mail without generating excessive heat or pollution. In addition, it is desirable to have a method and apparatus for sterilizing mail that may be used in the mail sorting process.

SUMMARY OF THE INVENTION

A method and apparatus for sterilizing mail according to the present invention includes a chamber defining an airtight enclosed space and having an entrance and exit through which mail may be conveyed. A vacuum pump is coupled to the chamber for withdrawing air from the chamber and an article of mail therein. This withdrawal of air reduces the air pressure in the chamber. An ozone gas generator is also coupled to the chamber and is capable of introducing ozone therein after all gases have been removed by the vacuum pump. Introducing ozone into the low pressure environment causes the ozone to permeate the article of mail very quickly as the ozone seeks to diffuse in even concentration throughout the chamber. Ozone is an unstable molecule that reacts with organic matter such as bacteria and viruses. This reaction destroys critical components of organisms, thereby being an effective sterilizing agent against anthrax within an article of mail. The highly reactive property of ozone makes sterilization very quick compared to other disinfectant methodologies. Following sterilization, the ozone is withdrawn from the chamber by another operation of the vacuum pump or with another fan such that the ozone is collected in an ozone filter. The filter includes a non-consumable catalyst such as manganese dioxide which converts the ozone into oxygen. The apparatus may be implemented using a single chamber or using multiple chambers connected by airlocks (multi-stage implementation).

Therefore, a general object of this invention is to provide a method and apparatus for sterilizing mail from anthrax or other pathogenic poisoning.

Another object of this invention is to provide a method and apparatus, as aforesaid, which sterilizes articles of mail quickly and without exposure of persons to harsh or harmful chemicals.

Still another object of this invention is to provide a method and apparatus, as aforesaid, which sterilizes articles of mail without damaging the articles of mail.

Yet another object of this invention is to provide a method and apparatus, as aforesaid, which sterilizes mail without generating excessive heat or pollution.

A further object of this invention is to provide a method and apparatus, as aforesaid, which may be integrated into a conventional mail sorting process.

Other objects and advantages of this invention will become apparent from the following description taken in connection with the accompanying drawings, wherein is set forth by way of illustration and example, embodiments of this invention.

DESCRIPTION OF THE PREFERRED EMBODIMENT

A method and apparatus for sterilizing mail against anthrax and other pathogens will now be described in detail with reference to FIGS. 1 through 4 of the accompanying drawings.

Figure 1:
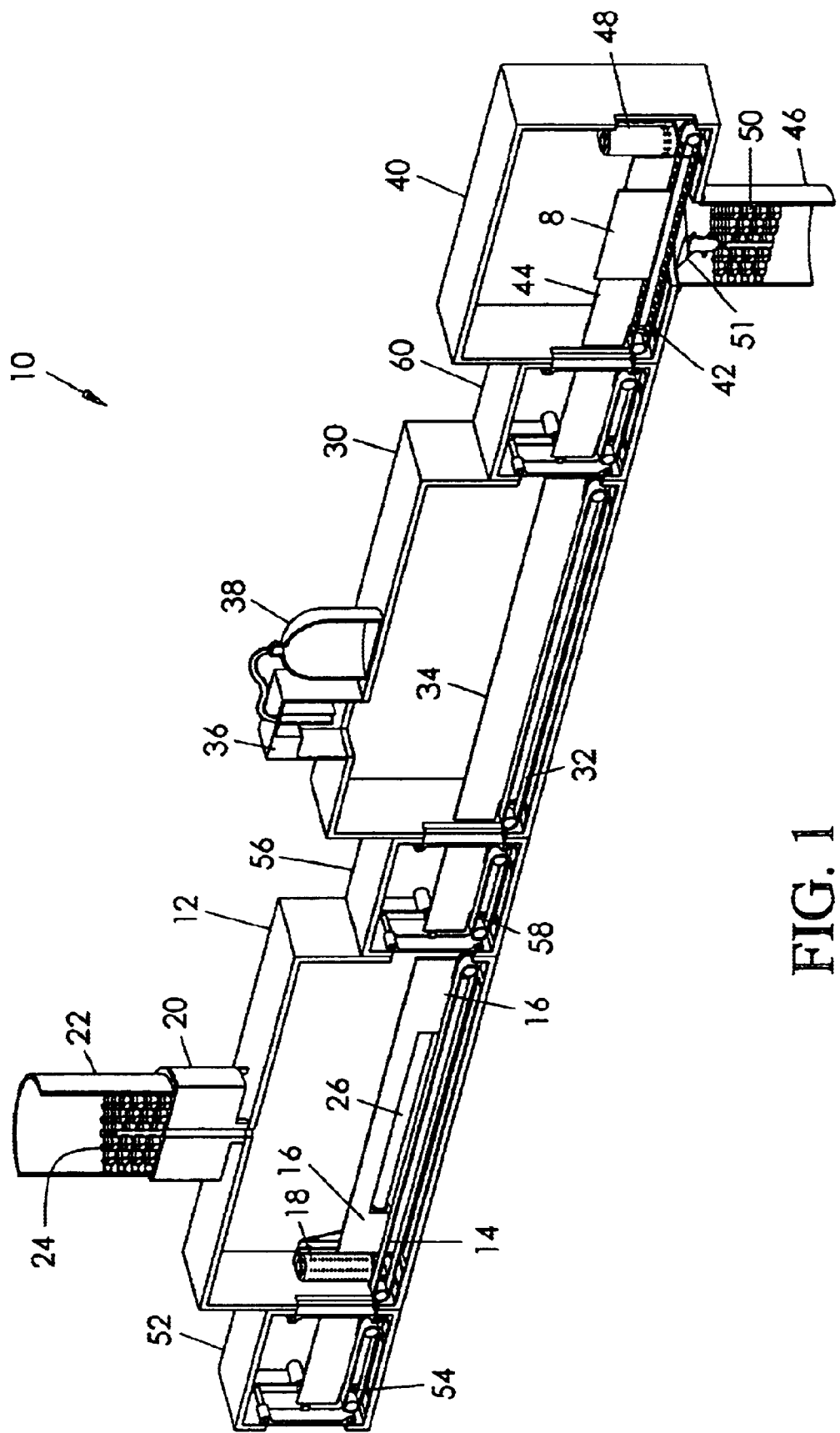
FIG. 1 is a perspective view, partially broken away, of a mail sterilization apparatus according to one embodiment of the present invention.
Figure 2:
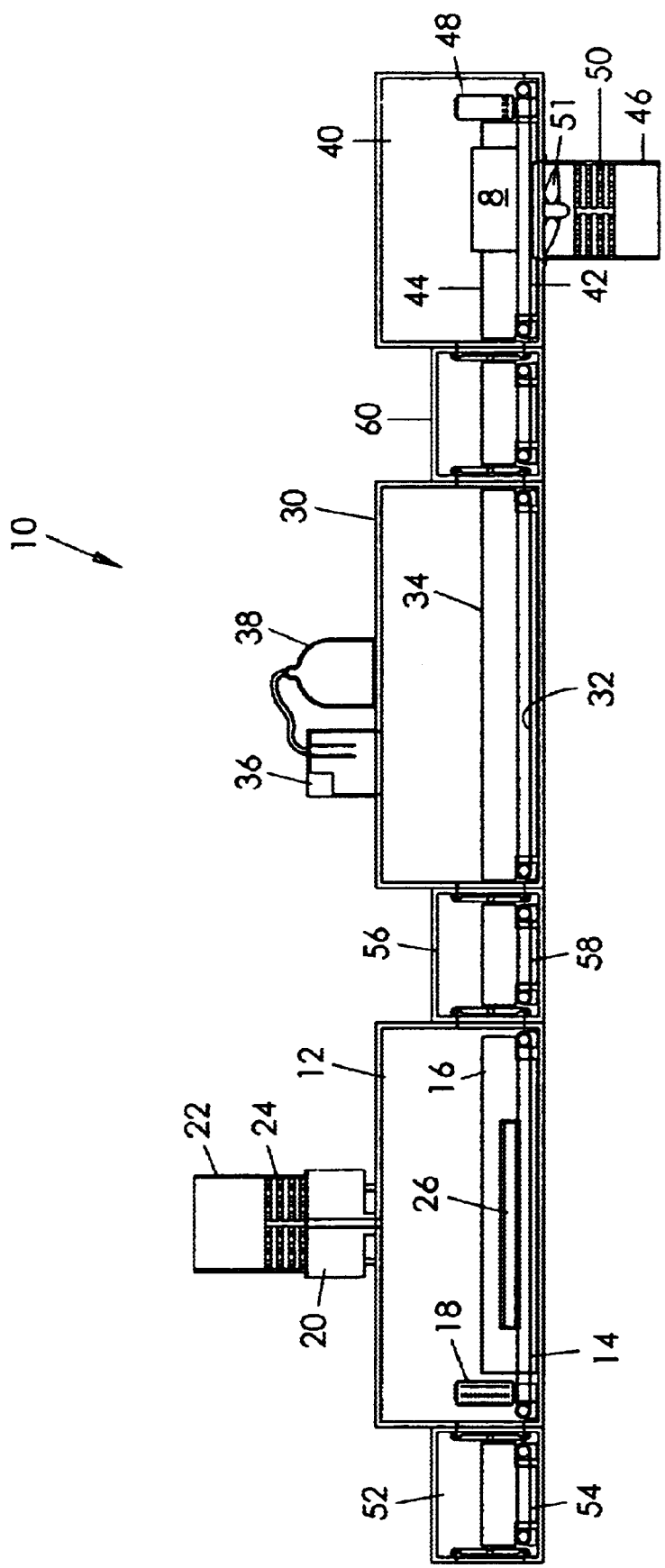
FIG. 2 is a side view of the mail sterilization apparatus as in FIG. 1.

A mail sterilizing apparatus 10 according to one embodiment of the present invention includes a multi-stage, multiple chamber construction (FIGS. 1 and 2). More particularly, the apparatus 10 includes a first chamber 12 having a rectangular or box-shaped configuration defining an enclosed interior space. The first chamber 12 may also be referred to as the vacuum chamber. The first chamber 12 includes entrance and exit openings at opposed ends thereof for entry and exit of articles of mail 8, respectively. A first conveyor 14 is positioned in the first chamber 12 and extends between the first chamber entrance and exit for moving an article of mail through the interior of the first chamber 12 along a first conveyance path. A first letter guide 16 extends along each side of the first conveyor 14 and is situated in an upstanding configuration for guiding an article of mail 8 along a first conveyance path defined by the first conveyor 14.

A first airlock 52 is coupled to the first chamber 12 adjacent the entrance thereto, the first airlock having doors that are selectively movable so as to seal or expose the entrance. A second airlock 56 is coupled to the first chamber 12 adjacent the exit therefrom, the second airlock 56 having doors that are selectively movable so as to seal or expose the exit. Of course, doors attached directly to the first chamber 12 for sealing or exposing the entrance and exit would also be a suitable construction. It is also understood that rotary airlocks would also be suitable rather than the two door airlocks shown. Therefore, the first chamber 12 is airtight when the first chamber entrance and exit are sealed. This is important as the air pressure within the first chamber 12 is modified as to be described in detail below. Each airlock 52, 56 further includes respective auxiliary conveyors 54, 58, respectively, for conveying an article of mail 8 therealong.

Preferably, a pair of perforation rollers 18 are mounted in upstanding configurations on opposed sides of the first chamber conveyor 14 adjacent the first chamber entrance, although a single perforation roller would be adequate. Thus, the perforation rollers 18 are positioned to bear against an article of mail 8 as it enters the first chamber 12. The perforation rollers 18 may be spring loaded so as to press against the article of mail 8 while accommodating various sizes of mail articles. Each perforation roller 18 includes a plurality of miniature pins or spikes for making almost imperceptible perforations in the article of mail 8 (i.e. in the envelope).

A vacuum pump 20 is coupled to the first chamber 12 and is in communication with the enclosed interior space thereof (FIGS. 1 and 2). An operation of the vacuum pump 20 withdraws air from the first chamber 12 and, more particularly, from the article of mail 8 being conveyed therethrough. The perforations placed in the article of mail 8 make this air withdrawal faster and more complete.

A first ozone filter 22 is connected to the vacuum pump 20 for receiving all air withdrawn from the first chamber 12 (FIG. 1). Preferably, the first ozone filter 22 includes a non-consumable catalyst 24 of manganese dioxide for converting any withdrawn ozone into oxygen before the air is exhausted into the environment surrounding the apparatus 10. Manganese dioxide is the preferred catalyst in that it is not consumed by reaction with ozone, decomposes ozone at ambient temperature, and decomposes ozone quickly.

One or more ultraviolet lamps 26 may be positioned within the first chamber 12. Ultraviolet light is a form of non-ionized radiation that is effective to irradiate and destroy pathogens upon exposure. Thus, exposing articles of mail to ultraviolet light sterilizes the outer surfaces thereof but does not penetrate envelopes or other packaging. However, sterilizing the outer surfaces of mail articles is still advantageous so as to prevent cross-contamination of the apparatus 10 itself or of postal workers.

The apparatus 10 includes a second chamber 30 connected to the first chamber 12 (FIG. 1). The second chamber 30 includes a construction substantially similar to the construction of the first chamber 12, including defining an entrance and exit. The second chamber 30 further includes a second conveyor 32 extending between the second chamber entrance and exit for moving an article of mail therethrough and includes second mail guides 34. More particularly, the second airlock 56 links the first and second chambers together. The second airlock 56 enables the article of mail 8 from which air has been withdrawn to maintain its low pressure as it exits the first chamber 12 and enters the second chamber 30. A third airlock 60 having a construction substantially similar to the airlocks previously described is coupled to the second chamber 30 adjacent the second chamber exit for selectively sealing the exit and making the second chamber airtight.

An ozone generator 36 is coupled to the second chamber 30 and is in communication with the enclosed interior space thereof. The ozone generator 36 is operatively connected to an oxygen tank 38 as its source of oxygen for ozone gas generation. Although the ozone generator 36 is capable of producing ozone using atmospheric air, a direct supply of oxygen can increase ozone concentration generation by over 400%. Once the article of mail 8 is received into the second chamber 30 and the second chamber 30 is sealed, the ozone generator 36 introduces a quantity of ozone gas into the second chamber 30. Of course, the second chamber 30 may already be filled with ozone when the article of mail 8 enters. The pressure differential between the article of mail 8 and the second chamber 30 causes the ozone to quickly diffuse and permeate the article of mail 8 and sterilize any microorganisms such as anthrax. Ozone is a powerful oxidant formed of three oxygen atoms ($O_3$). An ozone molecule is highly unstable and reacts with any organic matter including bacteria and viruses. Such a reaction is capable of splitting proteins and carbohydrates to damage critical components of organisms.

The apparatus 10 further includes a third chamber 40 connected to the second chamber 30 via the third airlock 60 (FIG. 1). The third chamber 40, which may also be referred to as the polishing chamber, includes a construction substantially similar to the construction of the chambers previously described, including having a third conveyor 42 and third mail guide 44. The third chamber 40 also defines a corresponding entrance and exit. In addition, a second ozone filter 46 is connected to the third chamber 40 for collecting ozone molecules remaining on the article of mail 8. The second ozone filter 46 includes a non-consumable catalyst 50 such as manganese dioxide for decomposing collected ozone into oxygen before exhausting it into the surrounding environment. A fan 51 is positioned within the third chamber 40 at the base of the second ozone filter 46 for drawing air from the third chamber 40 into the second ozone filter 46 (FIG. 2). It should be observed that the third conveyor 42 is perforated to allow air to be drawn more easily into the second ozone filter 46. It should be appreciated that air withdrawn from the first chamber 12 by the vacuum pump 20 may be funneled directly to the third chamber 40 such that only a single ozone filter would be needed.

At least one embossing roller 48 is mounted in the third chamber 40 adjacent the third chamber exit. The embossing roller 48 is positioned in an upstanding configuration adjacent a conveyance path defined by the third conveyor 42 such that articles of mail passing therealong will contact the embossing roller 48. The embossing roller 48 is suitable to leave a mark, impression, or indicia upon articles of mail with which it makes contact so as to indicate to mail recipients that the article of mail has completed the sterilization cycle. The article of mail 8 is then passed through the third chamber exit and may continue in a conventional mail sorting process, etc.

In use, the apparatus 10 may be configured as part of a flow-through mail sorting process or be used independently, e.g. in a corporate mailroom. A control panel (not shown)

configured to properly sequence operations may be used to control the apparatus 10 if the operations are not otherwise sequenced into an existing mail sorting process. An article of mail 8 is inserted or directed into the entrance of the first chamber 12 where it is conveyed along the first conveyor 14. Of course, the article of mail 8 may start by passing through the first airlock 52 although that is not essential. The article of mail 8 is perforated by the perforation rollers 18 and then the vacuum pump 20 may operate to withdraw air from the first chamber 12. Either sequentially or simultaneously with the vacuum pump operation, the outer surfaces of the article of mail 8 may be exposed to ultraviolet light from the ultraviolet lamps 26.

The lowered pressure is maintained as the article of mail 8 is conveyed through the second airlock 56 and into the second chamber 30. Ozone at substantially atmospheric pressure may be introduced into the second chamber 30 and the pressure differential causes the ozone to quickly permeate the article of mail 8. The diffusion of ozone within the article of mail sterilizes any microorganisms contained therein, such as anthrax spores. It should be appreciated that the ozone would eventually diffuse evenly into the article of mail in the absence of a pressure differential or perforations, but the pressure differential and perforations speed the process significantly. The article of mail 8 may then be conveyed through the third airlock 60 into the third chamber 40 where remaining ozone is drawn into the second ozone filter 50. This is the polishing stage which may conclude by embossing the article of mail 8 to indicate that it has completed the sterilization process.

Figure 3:
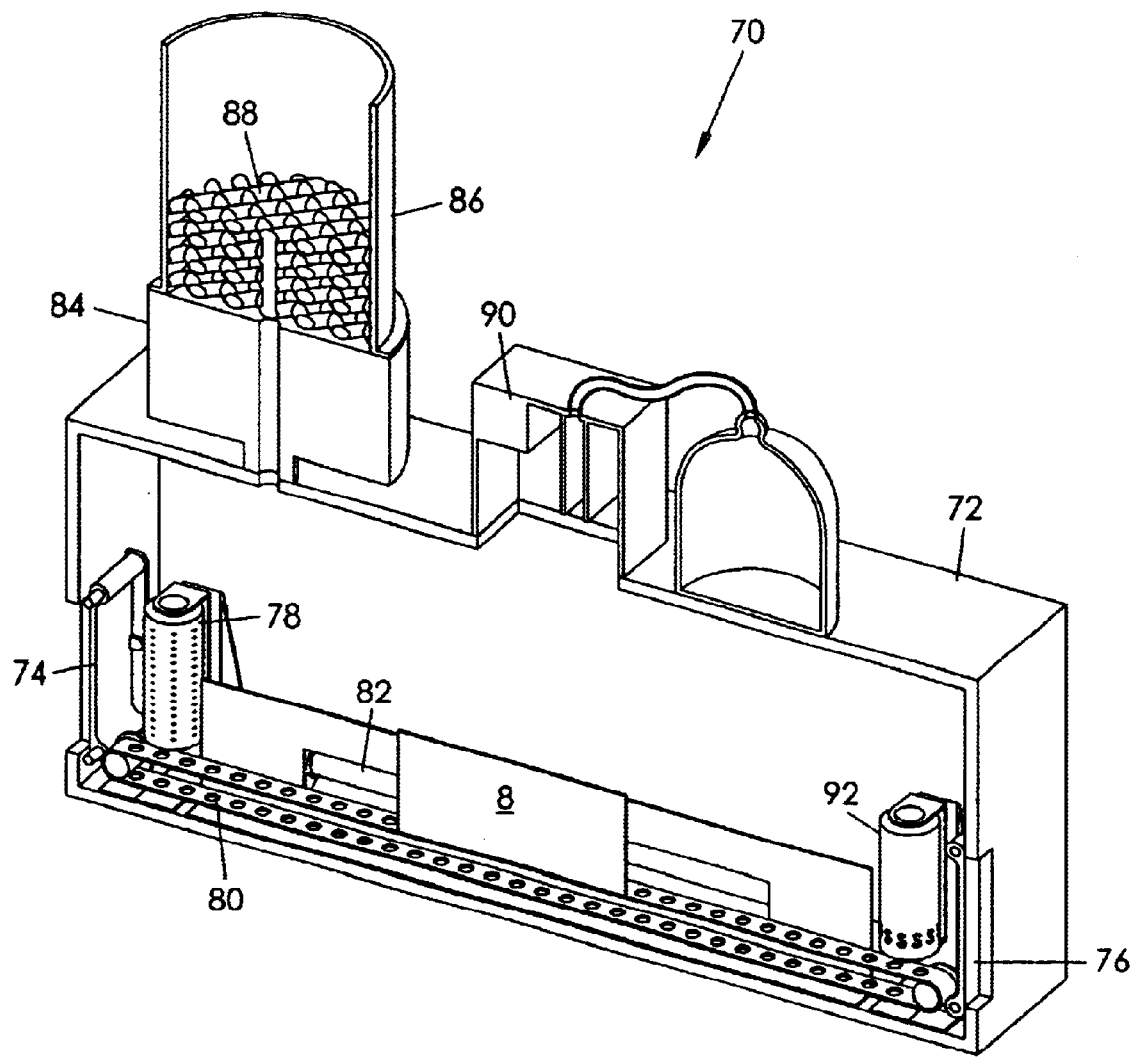
FIG. 3 is a perspective view of a mail sterilization apparatus, partially broken away, according to another embodiment of the present invention.
Figure 4:
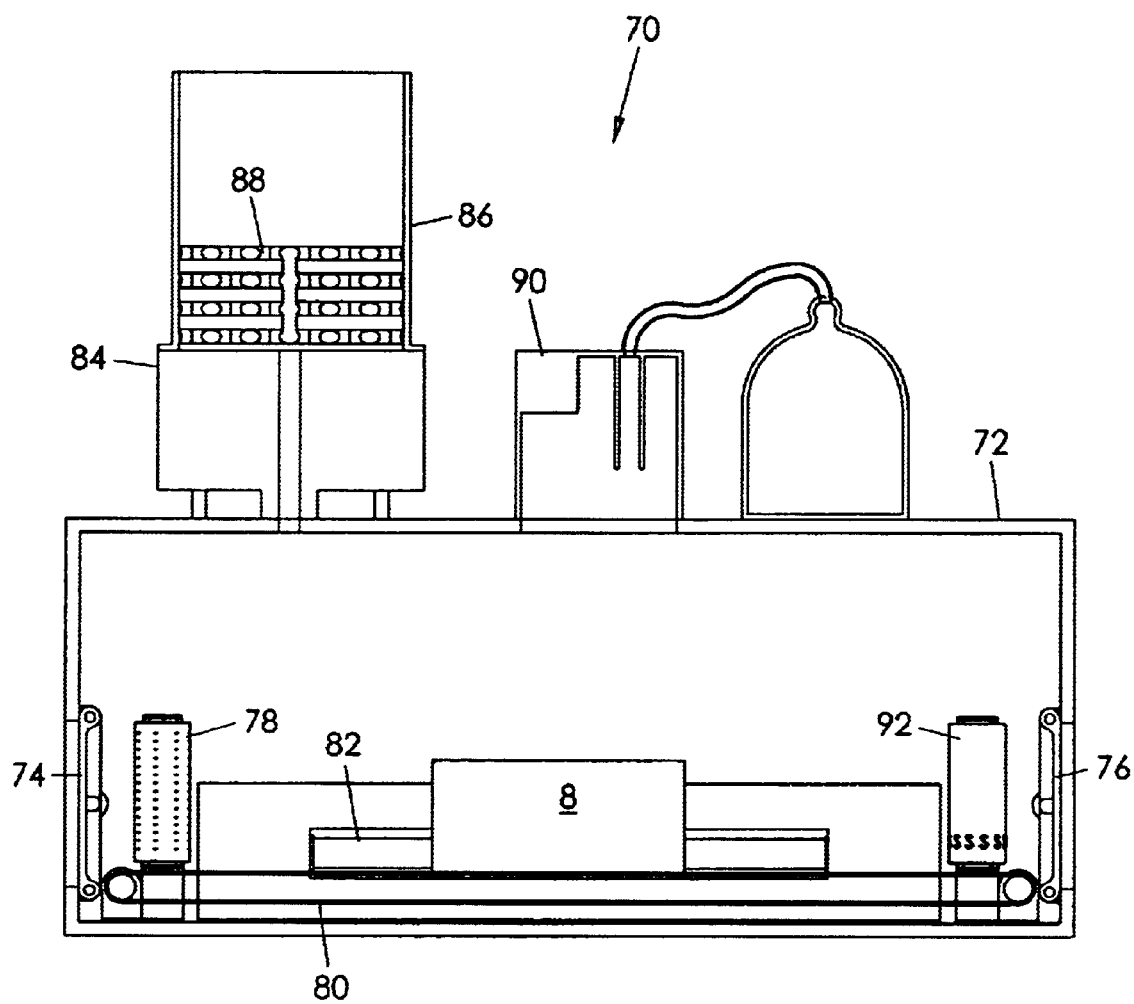
FIG. 4 is a side view of the mail sterilization apparatus as in FIG. 3.

A mail sterilization apparatus 70 according to another embodiment of the present invention is shown in FIGS. 3 and 4 and includes a construction substantially similar to the construction described above except as specifically noted below. The apparatus 70 according to this embodiment includes only a single chamber 72 but is capable of performing in a substantially similar manner as the apparatus first described. The single chamber 72 includes entrance 74 and exit 76 doors for sealing the entrance and exit openings as appropriate for the insertion or withdrawal of an article of mail 8. Perforation rollers 78 are mounted adjacent the entrance door 74 and along the path of a conveyor 80 for perforating the article of mail 8 as it is conveyed through the single chamber 72. One or more ultraviolet lamps 82 are positioned in the single chamber 72 along the path of the conveyor 80 for sterilizing the outer surfaces of an article of mail, in the manner described previously.

In the manner as described previously, a vacuum pump 84 is coupled to the single chamber 72 for withdrawing air from the single chamber 72 and from the article of mail 8. Withdrawn air is passed through an ozone filter 86 with a non-consumable catalyst 88 prior to being exhausted into the surrounding atmosphere. An ozone generator 90 is also coupled to the single chamber 72 for introducing ozone gas therein after operation of the vacuum pump 84. It is understood that the ozone is introduced at normal atmospheric pressure. Due to the pressure differential between the article of mail 8 and the ozone being introduced, the ozone quickly permeates the article of mail 8 for sterilizing any microorganisms therein. Following ozone sterilization, another operation of the vacuum pump 84 may evacuate the chamber of ozone before the article of mail 8 contacts an embossing roller 92 and exits the apparatus 70. This apparatus 70 is particularly convenient for use in a corporate mailroom, drop box, or residence.

In addition, it is contemplated that multiple tracks (e.g. conveyance paths) may be constructed within each chamber such that several articles of mail may be sterilized in parallel.

It is understood that while certain forms of this invention have been illustrated and described, it is not limited thereto except insofar as such limitations are included in the following claims and allowable functional equivalents thereof.

Having thus described the invention, what is claimed as new and desired to be secured by Letters Patent is as follows:

1. An apparatus for sterilizing an article of mail, comprising:
   a first chamber defining an enclosed space and having a first entrance and a first exit;
   a first conveyor extending between said first entrance and said first exit for moving the article of mail through said enclosed space of said first chamber along a first conveyance path;
   a vacuum pump coupled to said first chamber for withdrawing air from the article of mail being conveyed along said first conveyance path, said vacuum pump causing a reduced air pressure within said first chamber;
   a second chamber defining an enclosed space and having a second entrance and a second exit, said second chamber being positioned downstream from said first chamber;
   a first auxiliary conveyor for moving the article of mail downstream between said first exit and said second entrance;
   a second conveyor extending between said second entrance and said second exit for moving the article of mail through said enclosed space of said second chamber along a second conveyance path;
   an ozone generator coupled to said second chamber for introducing ozone into said second chamber as the article of mail is moved therethrough; and
   means in said ozone generator for substantially withdrawing ozone from said second chamber.

2. The apparatus as in claim 1 further comprising an ultraviolet lamp positioned in said first chamber along said first conveyance path for sterilizing outer surfaces of the article of mail being conveyed therealong.

3. The apparatus as in claim 1 further comprising:
   a third chamber defining an enclosed space and having a third entrance and a third exit, said third chamber being positioned downstream from said second chamber;
   a second auxiliary conveyor for moving the article of mail between said second exit and said third entrance;
   a third conveyor for moving the article of mail between said third entrance and said third exit along a third conveyance path; and
   an ozone filter coupled to said third chamber and having a non-consumable catalyst for converting ozone into oxygen.

4. The apparatus as in claim 1 further comprising an airlock positioned between said first and second chambers and surrounding said first auxiliary conveyor for retaining said reduced air pressure.

5. The apparatus as in claim 3 further comprising an airlock positioned between said second and third chambers and surrounding said second auxiliary conveyor for preventing unintended release of ozone as the article of mail is moved between said second and third chambers by said second auxiliary conveyor.

6. The apparatus as in claim 1 wherein:
   respective entrances and exits of said first and second chambers are selectively movable between open and closed configurations; and said first and second chambers are air-tight when said respective entrances and exits are in said closed configurations.

7. The apparatus as in claim 3 wherein:

said third entrance and said third exit of said third chamber are selectively movable between open and closed configurations; and said third chamber is air-tight when said third entrance and said third exit are at said closed configurations.

8. The apparatus as in claim 3 further comprising means positioned in said third chamber for applying an indicium upon the article of mail upon passage of the article of mail through said third chamber, said indicium being indicative of completion of a sterilization cycle.

9. The apparatus as in claim 3 wherein said nonconsumable catalyst is manganese dioxide.

10. The apparatus as in claim 1 further comprising a perforation roller pivotally mounted in said first chamber adjacent said first entrance and along said first conveyance path for contact with the article of mail, said perforation roller having a plurality of miniature pins arranged thereabout for perforating an outer surface of the article of mail as the article of mail is moved along said first conveyance path.

* * * * *